US011191917B2

United States Patent
Shelly

(10) Patent No.: US 11,191,917 B2
(45) Date of Patent: Dec. 7, 2021

(54) PRESSURE SUPPORT DEVICE AND METHOD OF PROVIDING AN ALERT FOR NON-EFFECTIVE PRESSURE COMPENSATION REGIMEN

(71) Applicant: KONINKLIJKE PHILIPS N.V., Eindhoven (NL)

(72) Inventor: Benjamin Irwin Shelly, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 485 days.

(21) Appl. No.: 16/143,675

(22) Filed: Sep. 27, 2018

(65) Prior Publication Data

US 2019/0099571 A1 Apr. 4, 2019

Related U.S. Application Data

(60) Provisional application No. 62/565,388, filed on Sep. 29, 2017.

(51) Int. Cl.
*A61M 16/00* (2006.01)
*A61B 5/08* (2006.01)
(Continued)

(52) U.S. Cl.
CPC ........... *A61M 16/024* (2017.08); *A61B 5/087* (2013.01); *A61B 5/0826* (2013.01);
(Continued)

(58) Field of Classification Search
CPC ........... A61B 1/233; A61B 2562/0204; A61B 2562/0219; A61B 2562/0247;
(Continued)

(56) References Cited

U.S. PATENT DOCUMENTS 5,148,802 A 9/1992 Sanders et al.
5,313,937 A 5/1994 Zdrojkowski
(Continued)

FOREIGN PATENT DOCUMENTS

DE 102015015439 A1 6/2017

OTHER PUBLICATIONS

Vroegop, Anneclaire V., et al. "Drug-induced sleep endoscopy in sleep-disordered breathing: Report on 1,249 cases." The Laryngoscope 124.3 (2014): 797-802.

(Continued)

*Primary Examiner* — Annette Dixon

(57) ABSTRACT

A pressure support device (4) for providing pressure support therapy to a patient includes a pressure generating system (6, 18) structured to generate pressure to provide pressure compensation to the patient via a patient circuit (12, 14), one or more sensors (22, 27, 28) structured to gather data indicative of disordered breathing events of the patient, and a processing unit (24) structured to control the pressure generating system to provide a pressure compensation regimen to the patient; to analyze outputs of the one or more sensors while pressure support therapy is provided to the patient to determine if the pressure compensation regimen provided to the patient is effective to relieve one or more disordered breathing events, and to output an alert if it is determined that the pressure compensation regimen provided to the patient is not effective in relieving the one or more disordered breathing events.

19 Claims, 7 Drawing Sheets

(51) Int. Cl.
  *A61B 5/00* (2006.01)
  *A61B 5/087* (2006.01)
  *A61B 5/11* (2006.01)

(52) U.S. Cl.
  CPC ....... *A61B 5/4848* (2013.01); *A61M 16/0003* (2014.02); *A61M 16/0051* (2013.01); *A61B 5/1116* (2013.01); *A61B 5/4809* (2013.01); *A61B 5/4818* (2013.01); *A61M 2016/003* (2013.01); *A61M 2016/0027* (2013.01); *A61M 2205/15* (2013.01); *A61M 2205/18* (2013.01); *A61M 2205/3331* (2013.01); *A61M 2205/3334* (2013.01); *A61M 2205/3576* (2013.01); *A61M 2210/06* (2013.01); *A61M 2210/1028* (2013.01); *A61M 2230/62* (2013.01)

(58) Field of Classification Search
  CPC ... A61B 5/0002; A61B 5/0022; A61B 5/0036; A61B 5/004; A61B 5/0086; A61B 5/015; A61B 5/02; A61B 5/0205; A61B 5/021; A61B 5/024; A61B 5/0402; A61B 5/0408; A61B 5/0476; A61B 5/0478; A61B 5/0488; A61B 5/0492; A61B 5/0496; A61B 5/08; A61B 5/0809; A61B 5/0826; A61B 5/0836; A61B 5/085; A61B 5/087; A61B 5/0875; A61B 5/097; A61B 5/103; A61B 5/11; A61B 5/1126; A61B 5/113; A61B 5/145; A61B 5/14503; A61B 5/14542; A61B 5/14551; A61B 5/14552; A61B 5/4806; A61B 5/4812; A61B 5/4815; A61B 5/4818; A61B 5/4836; A61B 5/6803; A61B 5/6814; A61B 5/6853; A61B 5/7232; A61B 5/7257; A61B 5/726; A61B 5/742; A61B 5/743; A61B 7/003; A61B 7/023; A61B 7/04; A61M 11/00; A61M 16/00; A61M 16/0003; A61M 16/0051; A61M 16/0057; A61M 16/0063; A61M 16/0066; A61M 16/0069; A61M 16/024; A61M 16/026; A61M 16/06; A61M 16/0616; A61M 16/0633; A61M 16/0683; A61M 16/0875; A61M 16/1045; A61M 16/105; A61M 16/107; A61M 16/20; A61M 16/202; A61M 16/204; A61M 16/209; A61M 2016/0021; A61M 2016/0027; A61M 2016/003; A61M 2016/0033; A61M 2016/0036; A61M 2016/0039; A61M 2202/0208; A61M 2202/0225; A61M 2205/02; A61M 2205/18; A61M 2205/3303; A61M 2205/3306; A61M 2205/3317; A61M 2205/332; A61M 2205/3324; A61M 2205/3331; A61M 2205/3334; A61M 2205/3355; A61M 2205/3375; A61M 2205/3553; A61M 2205/3561; A61M 2205/3569; A61M 2205/3584; A61M 2205/3592; A61M 2205/42; A61M 2205/50; A61M 2205/52; A61M 2205/581; A61M 2205/582; A61M 2205/6045; A61M 2205/70; A61M 2205/75; A61M 2205/8206; A61M 2205/8218; A61M 2205/8262; A61M 2209/088; A61M 2210/06; A61M 2210/0662; A61M 2230/005; A61M 2230/04; A61M 2230/06; A61M 2230/08; A61M 2230/10; A61M 2230/14; A61M 2230/18; A61M 2230/202; A61M 2230/205; A61M 2230/208; A61M 2230/30; A61M 2230/432; A61M 2230/435; A61M 2230/50; A61M 2230/60; A61M 2230/62; A61M 2230/63
  See application file for complete search history.

(56) References Cited

U.S. PATENT DOCUMENTS

| | | |
|---|---|---|
| 5,433,193 A | 7/1995 | Sanders et al. |
| 5,603,315 A | 2/1997 | Sasso, Jr. |
| 5,632,269 A | 5/1997 | Zdrojkowski |
| 5,803,065 A | 9/1998 | Zdrojkowski et al. |
| 6,029,664 A | 2/2000 | Zdrojkowski et al. |
| 6,539,940 B2 | 4/2003 | Zdrojkowski et al. |
| 6,626,175 B2 | 9/2003 | Jafari et al. |
| 6,675,797 B1 * | 1/2004 | Berthon-Jones ....... A61B 5/087 128/204.18 |
| 7,011,091 B2 | 3/2006 | Hill et al. |
| 7,942,824 B1 * | 5/2011 | Kayyali ............ A61M 16/0003 600/538 |
| 8,327,846 B2 * | 12/2012 | Bowditch ........... A61M 16/202 128/204.23 |
| 10,314,989 B2 * | 6/2019 | Goff ..................... A61M 16/20 |
| 2005/0076906 A1 * | 4/2005 | Johnson ............. A61M 16/024 128/204.21 |
| 2006/0037615 A1 | 2/2006 | Wilkinson et al. |
| 2007/0208269 A1 * | 9/2007 | Mumford .............. A61M 16/06 600/546 |
| 2011/0100366 A1 * | 5/2011 | Chou ................... A61B 5/6814 128/204.23 |
| 2012/0247472 A1 | 10/2012 | Lynch |
| 2015/0051449 A1 * | 2/2015 | Qiu ..................... A61B 5/6853 600/301 |
| 2015/0258290 A1 | 9/2015 | Landwehr |
| 2015/0327806 A1 | 11/2015 | Kezirian |
| 2016/0015916 A1 * | 1/2016 | Goff .................. A61M 16/1045 128/205.12 |
| 2016/0030689 A1 | 2/2016 | Landesberg |
| 2016/0346492 A1 | 12/2016 | Mulcahy et al. |

OTHER PUBLICATIONS

Pilaete, Karen, Joris De Medts, and Kathelijne Delsupehe. "Drug-induced sleep endoscopy changes snoring management plan very significantly compared to standard clinical evaluation." European Archives of Oto-Rhino-Laryngology 271.5 (2014).

Marques, Melania, et al. "Effect of Sleeping Position on Upper Airway Patency in Obstructive Sleep Apnea Is Determined by the Pharyngeal Structure Causing Collapse." Sleep 40.3 (2017).

Lee, Chul H., et al. "Changes in site of obstruction in obstructive sleep apnea patients according to sleep position: a DISE study." The Laryngoscope 125.1 (2015): 248-254.

Safiruddin, Faiza, Ioannis Koutsourelakis, and Nico de Vries. "Analysis of the influence of head rotation during drug-induced sleep endoscopy in obstructive sleep apnea." The Laryngoscope 124.9 (2014): 2195-2199.

Azarbarzin, A. et al., "Predicting epiglottic collapse in patients with obstructive sleep apnoea", European Respiratory Journal, vol. 50, No. 3, Sep. 2017.

* cited by examiner

Normal

Collapse at
soft-palate

Epiglott K
collapse

PRESSURE SUPPORT DEVICE AND METHOD OF PROVIDING AN ALERT FOR NON-EFFECTIVE PRESSURE COMPENSATION REGIMEN

CROSS-REFERENCE TO PRIOR APPLICATIONS

This application claims the benefit of U.S. Provisional Application No. 62/565,388, filed on 29 Sep. 2017. This application is hereby incorporated by reference herein.

BACKGROUND OF THE INVENTION

1. Field of the Invention

The present invention pertains to a pressure support device, and, in particular, to a pressure support device that determines effectiveness of a pressure compensation regimen.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether OSA, central, or mixed, which is a combination of OSA and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring. Thus, in diagnosing a patient with a breathing disorder, such as OSA, central apneas, or UARS, it is important to detect accurately the occurrence of apneas and hypopneas of the patient.

It is well known to treat sleep disordered breathing by applying a positive airway pressure (PAP) to the patient's airway using an airway pressure support system that typically includes a mask, a pressure generating device, and a conduit to deliver positive pressure breathing gas from the pressure generating device to the patient through the mask. This positive pressure effectively "splints" the airway, thereby maintaining an open passage to the lungs. In one type of PAP therapy, known as continuous positive airway pressure (CPAP), the pressure of gas delivered to the patient is constant throughout the patient's breathing cycle. It is also known to provide a positive pressure therapy in which the pressure of gas delivered to the patient varies with the patient's breathing cycle, or varies with the patient's effort, to increase the comfort to the patient. This pressure support technique is referred to as bi-level pressure support, in which the inspiratory positive airway pressure (IPAP) delivered to the patient is higher than the expiratory positive airway pressure (EPAP).

Pressure therapy is not always effective in treating sleep disordered breathing. However, a patient or medical provider may not be aware that or be aware why the pressure therapy provided to a patient is not effective in treating sleep disordered breathing of the patient.

SUMMARY OF THE INVENTION

A pressure support device for providing pressure support therapy to a patient comprises: a pressure generating system structured to generate pressure to provide pressure compensation to the patient via a patient circuit; one or more sensors structured to gather data indicative of disordered breathing events of the patient; and a processing unit structured to control the pressure generating system to provide a pressure compensation regimen to the patient; to analyze outputs of the one or more sensors while pressure support therapy is provided to the patient to determine if the pressure compensation regimen provided to the patient is effective to relieve one or more disordered breathing events, and to output an alert if it is determined that the pressure compensation regimen provided to the patient is not effective in relieving the one or more disordered breathing events.

A method of providing an alert for non-effective pressure compensation regimen comprises: providing a pressure compensation regimen to a patient; receiving data from one or more sensors (22, 27, 28) structured to gather data indicative of disordered breathing events of the patient; determining if one or more disordered breathing events of the patient are present based on the gathered data; determining if the pressure compensation regimen provided to the patient is effective to relieve one or more disordered breathing events; and outputting an alert if it is determined that the pressure compensation regimen provided to the patient is not effective in relieving the one or more disordered breathing events.

A non-transitory computer readable medium storing one or more programs, including instructions, which when executed by a computer, causes the computer to perform a method of providing an alert for non-effective pressure compensation regimen, the method comprising: providing a pressure compensation regimen to a patient; receiving data from one or more sensors (22, 27, 28) structured to gather data indicative of disordered breathing events of the patient; determining if one or more disordered breathing events of the patient are present based on the gathered data; determining if the pressure compensation regimen provided to the patient is effective to relieve one or more disordered breathing events; and outputting an alert if it is determined that the pressure compensation regimen provided to the patient is not effective in relieving the one or more disordered breathing events.

DETAILED DESCRIPTION OF EXEMPLARY EMBODIMENTS

Figure 1:
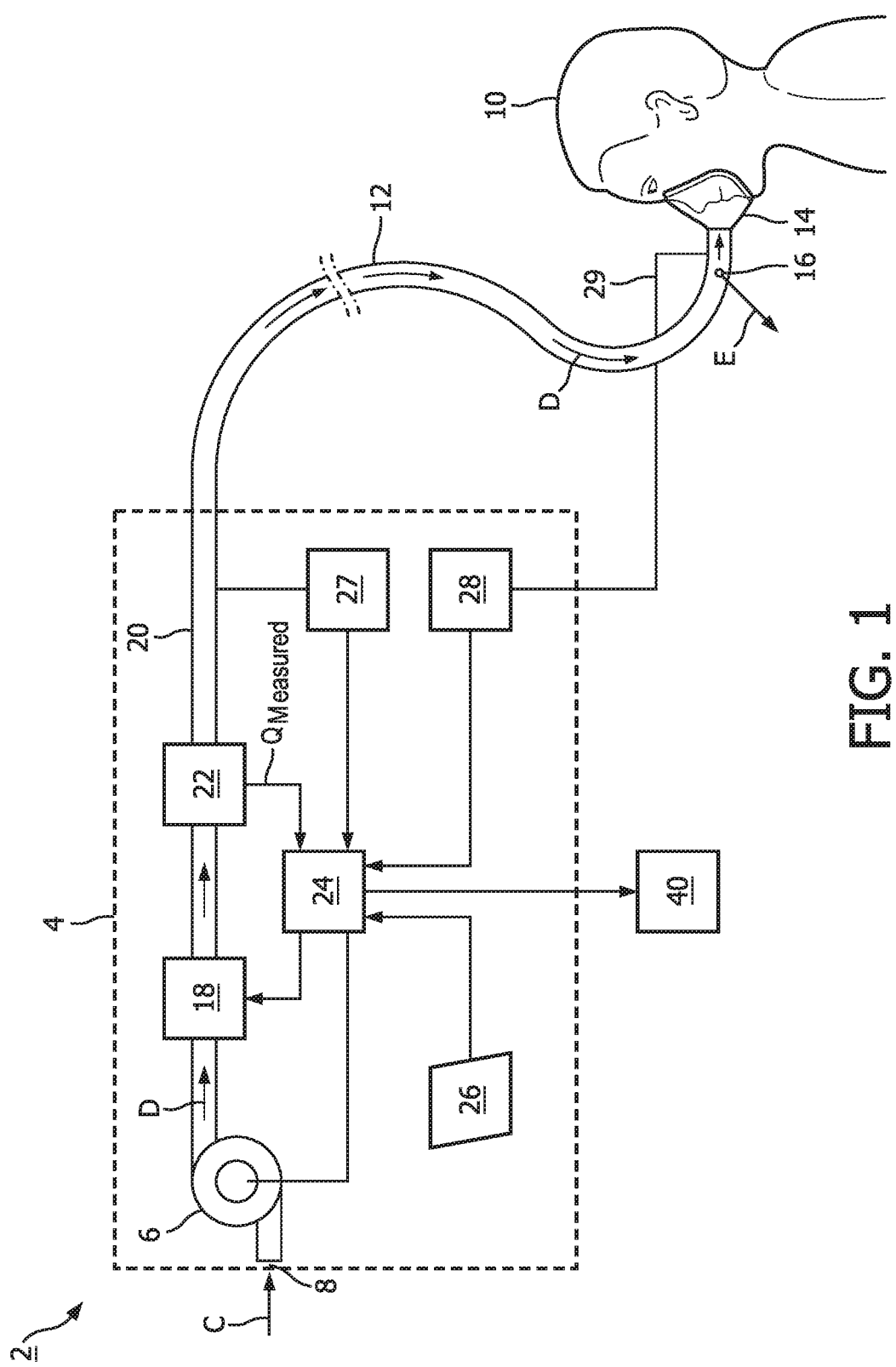
FIG. 1 is a schematic diagram of a pressure support system adapted to provide a regimen of respiratory therapy to a patient according to an exemplary embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 is a schematic diagram of an airway pressure support system 2 according to one particular, non-limiting exemplary embodiment in which the present invention may be implemented. Referring to FIG. 1, airway pressure support system 2 includes a pressure support device 4 which houses an airflow generator 6, such as a blower used in a conventional CPAP or bi-level pressure support device. Airflow generator 6 receives breathing gas, generally indicated by arrow C, from the ambient atmosphere through a filtered air inlet 8 provided as part of pressure support device 4, and generates a flow of breathing gas therefrom for delivery to an airway of a patient 10 at relatively higher and lower pressures, i.e., generally equal to or above ambient atmospheric pressure, to generate pressure to provide pressure compensation to patient 10 via a patient circuit 12, 14. In the exemplary embodiment, airflow generator 6 is capable of providing a flow of breathing gas ranging in pressure from 3-30 cmH2O. The pressurized flow of breathing gas from airflow generator 6, generally indicated by arrow D, is delivered via a delivery conduit 12 to a breathing mask or patient interface 14 of any known construction, which is typically worn by or otherwise attached to patient 10 to communicate the flow of breathing gas to the airway of patient 10. Delivery conduit 12 and patient interface device 14 are typically collectively referred to as the patient circuit.

Pressure support system 2 shown in FIG. 1 is what is known as a single-limb system, meaning that the patient circuit includes only delivery conduit 12 connecting patient 10 to pressure support system 2. As such, an exhaust vent 16 is provided in delivery conduit 12 for venting exhaled gases from the system as indicated by arrow E. It should be noted that exhaust vent 16 can be provided at other locations in addition to or instead of in delivery conduit 12, such as in patient interface device 14. It should also be understood that exhaust vent 16 can have a wide variety of configurations depending on the desired manner in which gas is to be vented from pressure support system 2.

The present concept also contemplates that pressure support system 2 can be a two-limb system, having a delivery conduit and an exhaust conduit connected to patient 10. In a two-limb system (also referred to as a dual-limb system), the exhaust conduit carries exhaust gas from patient 10 and includes an exhaust valve at the end distal from patient 10. The exhaust valve in such an embodiment is typically actively controlled to maintain a desired level or pressure in the system, which is commonly known as positive end expiratory pressure (PEEP).

Furthermore, in the illustrated exemplary embodiment shown in FIG. 1, patient interface 14 is a nasal/oral mask. It is to be understood, however, that patient interface 14 can include a nasal mask, nasal pillows, a tracheal tube, an endotracheal tube, or any other device that provides a suitable gas flow communicating function. Also, for purposes of the present invention, the phrase "patient interface" can include delivery conduit 12 and any other structures that couple the source of pressurized breathing gas to patient 10.

In the illustrated embodiment, pressure support system 2 includes a pressure controller in the form of a valve 18 provided in internal delivery conduit 20 provided in a housing of pressure support device 4. Valve 18 controls the pressure of the flow of breathing gas from airflow generator 6 that is delivered to patient 10. For present purposes, airflow generator 6 and valve 18 are collectively referred to as a pressure generating system because they act in concert to generate and control the pressure and/or flow of gas delivered to patient 10. However, it should be apparent that other techniques for controlling the pressure of the gas delivered to patient 10, such as varying the blower speed of gas flow generator 6, either alone or in combination with a pressure control valve, are contemplated by the present invention. Thus, valve 18 is optional depending on the technique used to control the pressure of the flow of breathing gas delivered to patient 10. If valve 18 is eliminated, the pressure generating system corresponds to airflow generator 6 alone, and the pressure of gas in the patient circuit is controlled, for example, by controlling the motor speed of airflow generator 6.

Pressure support system 2 further includes a flow sensor 22 that measures the flow of the breathing gas within delivery conduit 20 and delivery conduit 12. In the particular embodiment shown in FIG. 1, flow sensor 22 is interposed in line with delivery conduits 20 and 12, most preferably downstream of valve 18. Pressure support system 2 additionally includes a pressure sensor 27 that detects the pressure of the pressurized fluid in delivery conduit 20. While the point at which the flow is measured by flow sensor 22 and the pressure is measured by pressure sensor 27 are illustrated as being within pressure support device 4, it is to be understood that the location at which the actual flow and pressure measurements are taken may be anywhere along delivery conduits 20 or 12. The flow of breathing gas measured by flow sensor 22 and the pressure detected by pressure sensor 27 are provided to processing unit 24 to determine the flow of gas at patient 10 ($Q_{PATIENT}$). [25] Techniques for calculating $Q_{PATIENT}$ are well known, and take into consideration the pressure drop of the patient circuit, known leaks from the system, i.e., the intentional exhausting of gas from the circuit as indicated by arrow E in FIG. 1, and unknown leaks from the system, such as leaks at the mask/patient interface. The present invention contemplates using any known or hereafter developed technique for calculating leak flow, and using this determination in calculating $Q_{PATIENT}$ using measured flow and pressure. Examples of such techniques are taught by U.S. Patent Nos. 5,148,802; 5,313,937; 5,433,193; 5,632,269; 5,803,065; 6,029,664; 6,539,940; 6,626,175; and 7,011,091, the contents of each of which are incorporated by reference into the present invention.

Of course, other techniques for measuring the respiratory flow of patient 10 are contemplated by the present invention, such as, without limitation, measuring the flow directly at patient 10 or at other locations along delivery conduit 12, measuring patient flow based on the operation of gas flow generator 6, and measuring patient flow using a flow sensor upstream of valve 18.

In some non-limiting embodiments of the disclosed concept, pressure support system 2 also includes a proximal pressure sensor 28 that is in fluid communication with a point along delivery conduit 12. For example and without limitation, proximal pressure sensor 28 may be in fluid communication with a point on delivery conduit 12 near patient interface device 14 via a probe 29 connected between proximal pressure sensor 28 and the point on delivery conduit 12. Proximal pressure sensor 28 facilitates measuring pressure proximate the point on delivery conduit 12 and provide the measured proximal pressure to processing unit 24. It will be appreciated that in some exemplary embodiments, proximal pressure sensor 28 may be omitted.

While the flow sensor 22, pressure sensor 27, and proximal pressure sensor 28 have been shown in conjunction with the pressure support system 2 illustrated in FIG. 1, it will be appreciated by those having ordinary skill in the art that other types of sensors may also be employed in conjunction with pressure support system 2 without departing from the scope of the disclosed concept. For example and without limitation, a temperature sensor may be used to measure temperature, a proximity/contact sensor may be used to sense contact between patient 10 and components of the patient interface. Other types of sensors that may be employed in conjunction with pressure support system include, for example and without limitation, location sensors (e.g., global positioning system sensors) to determine a location of pressure support system 2, light sensors to sense light, accelerometers to sense acceleration and/or movement, microphones to sense sound, identification sensors such as radio frequency identification (RFID) sensors to sense identification information from RFID chips attached to components, heart rate sensors, SpO2 monitors, an EEG sensor or sensors, or body position sensors 36 (shown in FIG. 2) to sense a sleeping position of patient 10. The body position sensor 36 may be an accelerometer which would serve to provide information on body orientation. It will be appreciated that the foregoing examples of types of sensors that may be employed in conjunction with pressure support system 2 is not exhaustive and other types of sensors may also be employed without departing from the scope of the disclosed concept.

Processing unit 24 includes a processing portion which may be, for example, a microprocessor, a microcontroller or some other suitable processing device, and a memory portion that may be internal to the processing portion or operatively coupled to the processing portion and that provides a storage medium for data and software executable by the processing portion for controlling the operation of pressure support system 2. Processing unit 24 is structured to receive output of one or more sensors structured to gather data indicative of disordered breathing events of patient 10. The one or more sensors structured to gather data indicative of disordered breathing events may include, without limitation, flow sensor 22, pressure sensor 27, and proximal pressure sensor 28. However, it will be appreciated that other types of sensors may be used to gather data indicative of disordered breathing events. The disordered breathing events may include, without limitation, obstructive apneas. However, the disordered breathing events may include other types of disordered breathing events such as, without limitation, obstructive and central hypopneas, effort related arousals, non-obstructive apneas, etc. Processing unit 24 is also structured to control the pressure generating unit to provide a pressure compensation regimen to patient 10. Processing unit 24 may control the pressure generating unit by, for example and without limitation, controlling airflow generator 6 to change its motor speed and/or controlling valve 18 to change the pressure of the flow of breathing gas provided to patient 10. The pressure compensation regimen may be, for example, a pattern of changing pressures of the flow of breathing gas provided to patient 10. The pressure compensation regimen may also be reactively changed in response to detecting disordered breathing events.

Processing unit 24 is further structured analyze output of the one or more sensors structured to gather data indicative of disordered breathing events by, for example, determining when disordered breathing events are occurring in patient 10 based on outputs of the one or more sensors structured to gather data indicative of disordered breathing events. For example and without limitation, processing unit 24 may determine that patient 10 is experiencing an obstructive apnea event based on output of flow sensor 22, pressure sensor 27, proximal pressure sensor 28, and/or other sensors. Processing unit 24 is further structured to analyze outputs of the one or more sensors to determine whether the pressure compensation regimen provided to the patient is effective to relieve the disordered breathing events. For example and without limitation, processing unit 24 may determine that the pressure compensation provided to patient 10 is not effective when the disordered breathing events persist through the pressure compensation regimen (e.g., without limitation, the disordered breathing events persist longer than a predetermined amount of time).

Processing unit 24 may also determine that the pressure compensation regimen provided to patient 10 is not effective using other methods. For example and without limitation, processing unit 24 may change characteristics of the pressure compensation regimen (e.g., without limitation, changing pressure of the breathing gas provided to patient 10) provided to patient 10 and may determine that the pressure compensation regimen provided to patient 10 when the disordered breathing event persists through a predetermined number of changes to the pressure compensation regimen. In another example embodiment, one or more of the sensors may sense an airflow waveform for a number of breaths of patient 10. Based on the airflow waveform, processing unit 24 may determine that the disordered breathing event is an epiglottic collapse and, in response to determining that an epiglottic collapse is present, processing unit 24 may determine that the pressure compensation regimen is not effective and output the alert.

Pressure support devices such as pressure support device 4 are generally effective in treating disordered breathing events such as obstructive apnea through pressure support therapy. However, approximately 5% of patients have obstructive apneas that a pressure-resistant (i.e. apneas where the airway is closed, but not treatable with higher pressure compensation). In these types of patients, pressure support therapy alone will not be able to effectively treat these patients. Between 15-20% of obstructive apnea patients may have an airway collapse at the epiglottis. Pressure support therapy may be able to dilate the airway enough to alleviate secondary epiglottic collapse that is mediated by upstream airway resistance or by physical pressure by the tongue base. A primary epiglottic collapse may not be treatable with pressure support therapy. While pressure support therapy for patients that suffer from pressure-resistant obstructive apneas and/or epiglottic collapse may not be effective, positional therapy (e.g., changing the sleeping position of the patient and/or having the patient sleep in a non-supine position) may be effective to treat these conditions. However, if pressure support therapy has not been effective in relieving disordered breathing events, patient 10 or a medical provider should be alerted so that they can consider trying positional therapy as an alternative.

To this end, processing unit 24 is structured to output an alert in response to determining that the pressure compensation regimen provided to patient 10 has not been effective in relieving the disordered breathing event. The alert may be, for example and without limitation, an electronic signal that it sent to another device to provide a visual, audible, or tactile indication. In some example embodiments of the disclosed concept, the alert is used to alert patient 10 to change position. For example and without limitation, the alert cause an indicator 40 to provide a tactile indication (e.g., without limitation, a vibration) to alert patient 10 to change position (e.g., without limitation, to move off his/her back). It will be appreciated that indicator 40 may provide visual and/or audible indications in some embodiments. Indicator 40 may be, without limitation, a display, light, or other type of visual indicator, a buzzer, speaker, or other type of audible indicator, and/or a vibrator or other type of tactile indicator. It will be appreciated that pressure support system 2 may include more than one indicator 40. For example and without limitation, pressure support system 2 may include two indicators 40, one providing a visual indication and one providing a tactile indication. Indicator 40 is structured to output the indication in response to processing unit 24 outputting the alert.

In some example embodiments, the alert is used to alert patient 10 or a medical provider and suggest trying positional therapy. In some example embodiments, processing unit 24 may output the alert to an external device such as, without limitation, mobile device or a computer. In some example embodiments, the external device may be accessible by a medical provider (e.g. without limitation, the external device may be the medical provider's computer or mobile device). The alert may include a suggestion to try positional therapy. Patient 10 and/or medical provider may thus be alerted when the pressure compensation regimen is not effective in relieving the disordered breathing event and patient 10 and/or medical provider may consider implementing positional therapy as an alternative. It will be appreciated that in some example embodiments, the alert may not be outputted immediately, but rather may be output at a later time such as the next day. The alert may be included in a usage report, displayed with indicator 40 or a user interface of pressure support system, accessible via an application on a mobile device or other electronic device, or any other method so as to bring attention to patient 10 and/or a medical provider that the pressure compensation regimen has not been effective to relieve the disordered breathing events.

An input/output device 26 is provided for setting various parameters used by pressure support system 2, as well as for displaying and outputting information and data to a user, such as a clinician or caregiver. In some example embodiments, input/output device 26 may serve as an indicator and provide an indication when processing unit 24 outputs the alert.

Figure 2:
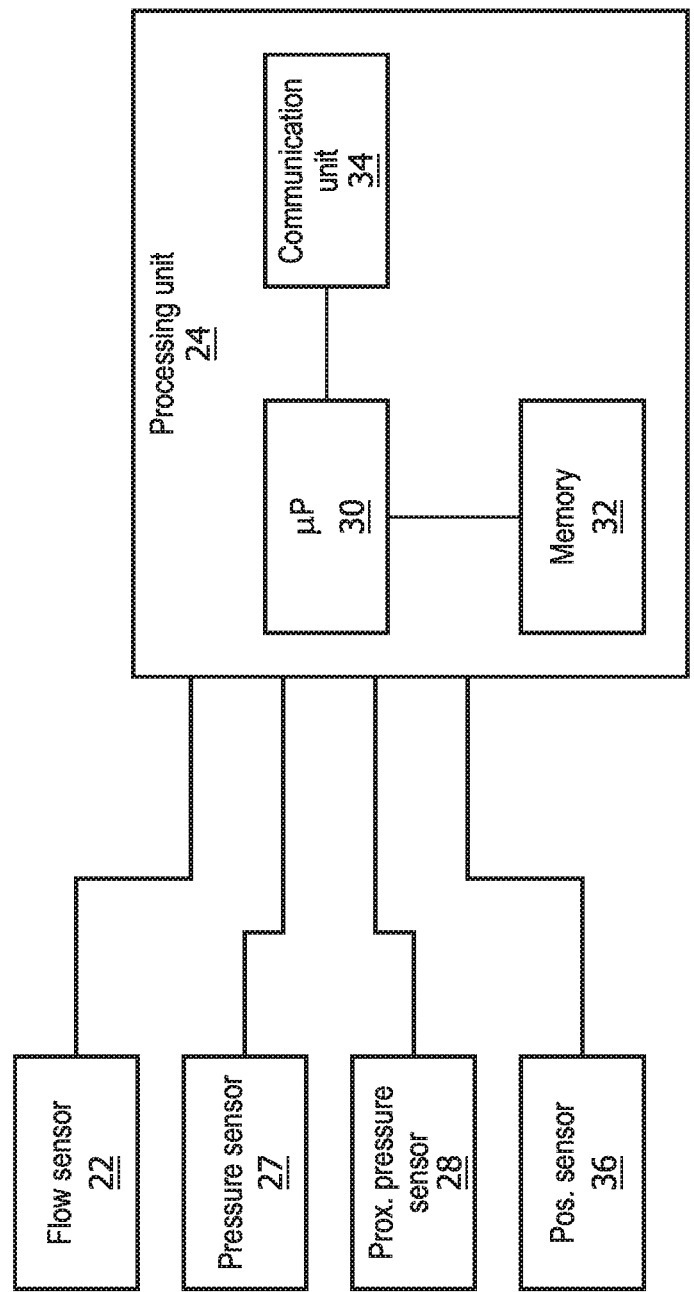
FIG. 2 is a schematic diagram of a processing unit according to an exemplary embodiment of the disclosed concept.

In some example embodiments, processing unit 24 may determine a body or head position of patient 10 based on the outputs of the one or more sensors, such as body position sensor 36 (shown in FIG. 2). Processing unit 24 may further determine whether patient 10 is in a supine position based on the output of body position sensor 36. In some example embodiments, processing unit 24 only output the alert if patient 10 is in the supine position. In this case, the alert may not be beneficial to patient 10 if patient 10 is already in a non-supine position. In some example embodiments, information from body position sensor 36 can be used to determine that patient 10 is a good candidate for positional therapy only (e.g., no longer needs pressure support therapy if he/she will sleep in a non-supine position) or that pressure (or pressure range) could be significantly decreased if positional therapy was used.

In some example embodiments, processing unit 24 is structured to determine when patient 10 has aroused from sleep. Processing unit 24 may determine when patient 10 has aroused from sleep based on output of one or more of the sensors. Processing unit 24 may use characteristics such as, without limitation, differences between breath waveforms such as differences in peak airflow, flow shape, tidal volume, ration of inhalation to exhalation, variability in breath rate, breath period, or other airflow-based parameters to determine when patient 10 has aroused. Changes in average volume of air inspired/expired per minute may also be considered to determine when patient 10 has aroused. Outputs of sensors such as an accelerometer, microphone, heart rate sensor, proximity sensor, etc. may also be used to determine when patient 10 has aroused. Processing unit 24 may wait until patient 10 has aroused before outputting the alert. In some example embodiments, processing unit 24 may output the alert upon determining that the pressure compensation regimen is not effective. The alert may be of a nature that it arouses patient 10 (e.g., an audible and/or tactile indication). It will be appreciated that the determination of waiting to output the alert or immediately outputting the alert may be based on the severity of the disordered breathing event, the extent of the pressure compensation regimen, the severity of patient's 10 condition, and/or the type of pressure compensation regimen.

It will be appreciated that pressure support device 4 may include additional components that are not illustrated in the schematic diagram of FIG. 1. For example and without limitation, pressure support device 4 may include a filter to filter breathing gas provided to patient 10 and a humidifier to humidify breathing gas provided to patient 10.

In the illustrated, non-limiting exemplary embodiment of the present invention, airway pressure support system 2 essentially functions as a CPAP pressure support system and pressure support device 4 provides functions of a CPAP base unit. Pressure support system 2, therefore, includes all of the capabilities necessary in such systems in order to provide appropriate CPAP pressure levels to patient 10. This includes receiving the necessary parameters, via input commands, signals, instructions or other information, for providing appropriate CPAP pressure, such as maximum and minimum CPAP pressure settings. It should be understood that this is meant to be exemplary only, and that other pressure support methodologies, including, but not limited to, BiPAP AutoSV, AVAPS, Auto CPAP, and BiPAP Auto, are within the scope of the present invention.

FIG. 2 is a block diagram of processing unit 24 in accordance with a non-limiting exemplary embodiment of the disclosed concept. Processing unit 24 includes a processor 30, a memory 32, and a communication unit 34. Processor 30 may form all or part of a processing portion which may be, for example, a microprocessor, a microcontroller or some other suitable processing device. Memory 32 may form all or part of a memory portion that may be internal to the processing portion or operatively coupled to the processing portion and provide a storage medium for data and software executable by the processing portion for implementing functionality of processing unit 23 and controlling the operation of pressure support system 2. Memory 32 can be any of one or more of a variety of types of internal and/or external storage media such as, without limitation, RAM, ROM, EPROM(s), EEPROM(s), FLASH, and the like that provide a storage register, i.e., a machine readable medium, for data storage such as in the fashion of an internal storage area of a computer, and can be volatile memory or nonvolatile memory.

Communication unit 34 may provide for communication between processing unit 24 and other components of pressure support device 4, components of the patient circuit, or other external devices. For example and without limitation, communication unit 34 may facilitate communication with various sensors such as flow control sensor 22. Communication unit 34 may also facilitate communication with external devices. For example and without limitation, communication unit 34 may facilitate communication with electronic devices such as a phone, tablet, computer, or other devices directly or via a network. Communication facilitated by communication unit 34 may allow processing unit 24 to send and/or receive data from the component or device it communicates with.

As previously described, processing unit 24 receives outputs from one or more sensors such as, for example and without limitation, flow sensor 22, pressure sensor 27, proximal pressure sensor 28, and body position sensor 36. Although flow sensor 22, pressure sensor 27, proximal pressure sensor 28, and body position sensor 36 are shown, it will be appreciated that one or more of these sensors may be omitted without departing from the scope of the disclosed concept. It will also be appreciated that processing unit 24 may receive outputs from one or more other types of sensors that are not shown in FIG. 2. For example and without limitation, processing unit 24 may receive outputs from one or more of a temperature sensor, a proximity/contact sensor, location sensors, microphones, or identification sensors.

Figure 3:
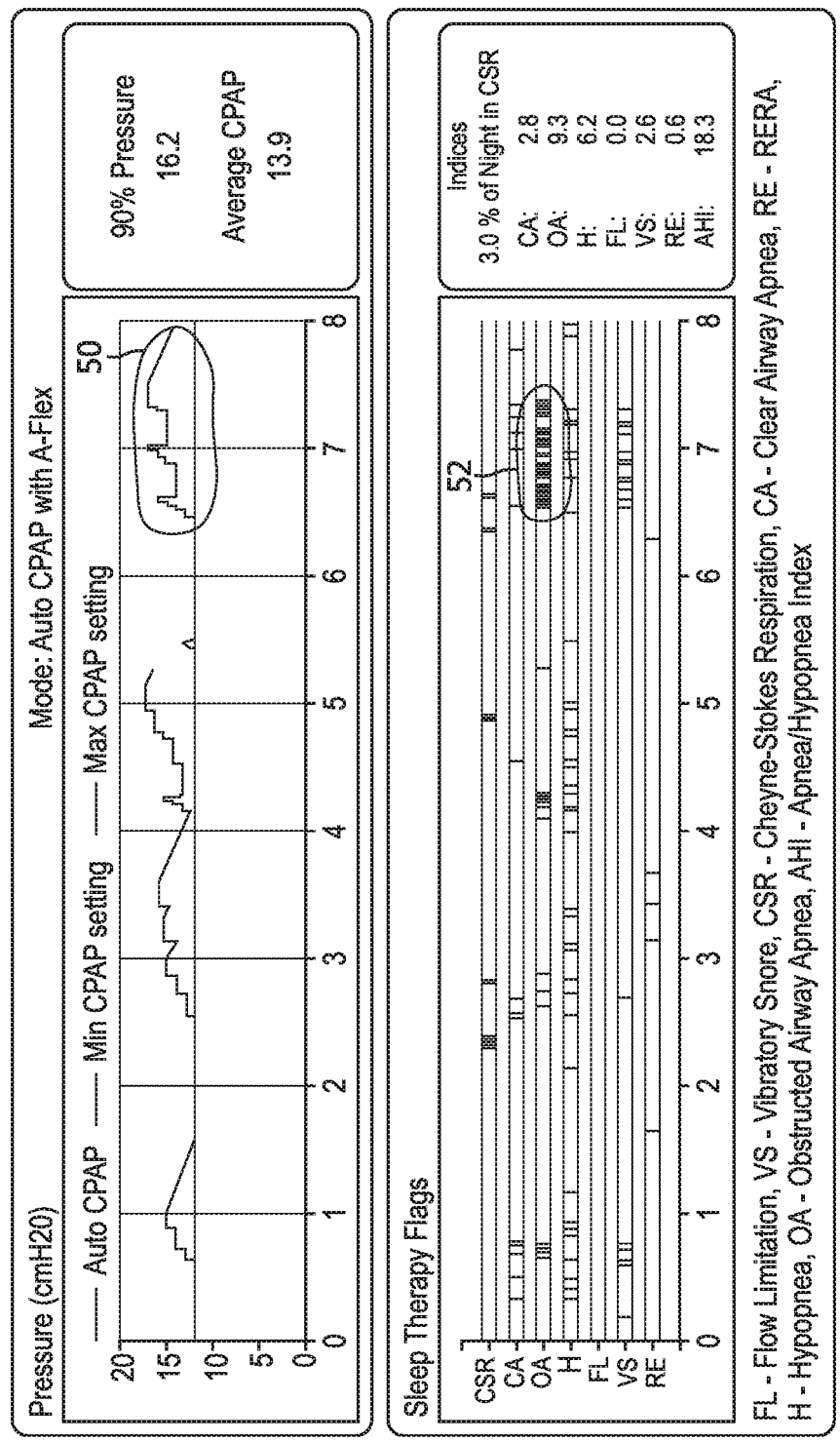
FIGS. 3-5 are graphs of pressure compensation regimens and corresponding disordered breathing events in accordance with example embodiments of the disclosed concept.

FIG. 3 is a graph of a pressure compensation regimen and detected disordered breathing events in accordance with an example embodiment of the disclosed concept. The pressure compensation regimen may be provided by pressure support device 4 and the disordered breathing events may be detected by processing unit 24 based on outputs of one or more sensors such as flow sensor 22, pressure sensor 27, and/or proximate pressure sensor 28. Highlighted in FIG. 3 are a pressure compensation regimen 50 and a series of disordered breathing events 52. FIG. 3 covers a period of 8 hours. From hours 0 to about 6.5, the pressure compensation regimen is primarily effective in relieving disordered breathing events that arise. However, at about hour 6.5 disordered breathing events 52 (e.g., obstructive apneas) are detected and persists until after hour 7. During this period, pressure compensation regimen 50 includes three series of increases in pressure, each containing three pressure increases, but disordered breathing events 52 persist until at least the third series of increases in pressure. While disordered breathing events 52 eventually subside, it is more likely responsive to a change in the patient condition (e.g., sleep state or body position) rather than an effect of the pressure compensation regimen. In some example embodiments, processing unit 24 may determine that the pressure compensation regimen is not effective and output the alert based on pressure compensation regimen 50 and disordered breathing events 52 from about hour6.5 to after hour 7. For example, processing unit 24 may determine that the pressure compensation regimen is not effective based on the persistence of the disordered breathing events for a predetermined period of time and/or based on the lack of effectiveness of changes in the pressure compensation regimen.

Figure 4:
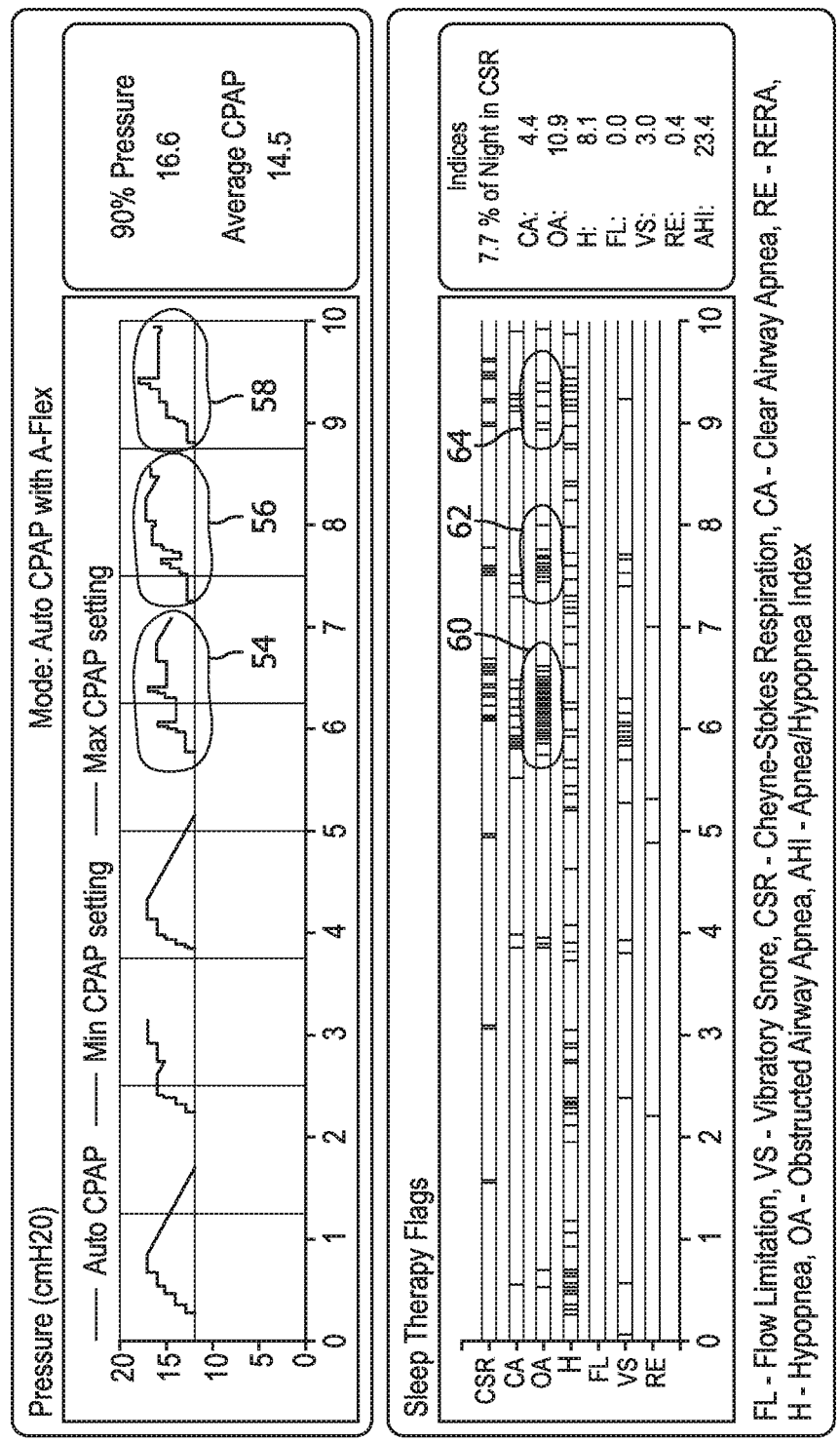

Similar to FIG. 3, FIG. 4 is a graph of a pressure compensation regimen and detected disordered breathing events in accordance with an example embodiment of the disclosed concept. The pressure compensation regimen may be provided by pressure support device 4 and the disordered breathing events may be detected by processing unit 24 based on outputs of one or more sensors such as flow sensor 22, pressure sensor 27, and/or proximate pressure sensor 28. Highlighted in FIG. 4 are a pressure compensation regimens 54, 56, and 58 and corresponding series of disordered breathing events 60, 62, and 64. Similar to FIG. 3, the highlighted disordered breathing events 60, 62, and 64 in FIG. 4 persist through changes in their corresponding pressure compensation regimens 54, 56, and 58. The highlighted pressure compensation regimens 54, 56, and 58 and corresponding disordered breathing events 60, 62, and 64 in FIG. 4 are additional examples of patterns which may trigger processing unit 24 to output the alert.

Figure 5:
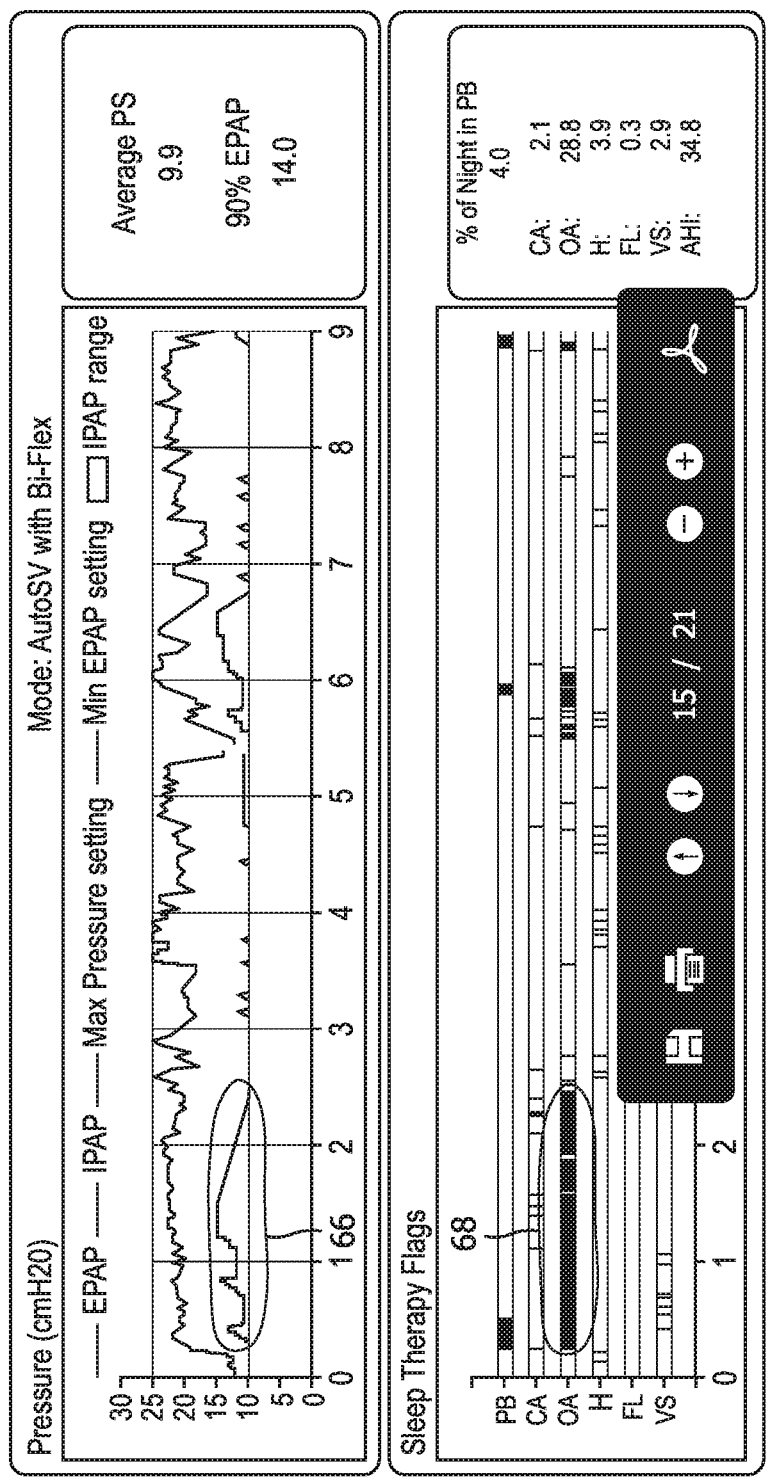

Similar to FIGS. 3 and 4, FIG. 5 is a graph of a pressure compensation regimen and detected disordered breathing events in accordance with an example embodiment of the disclosed concept. However, the graph in FIG. 5 corresponds to a pressure compensation regimen provided by an adaptive servo ventilation (ASV) device, rather than a CPAP device. The pressure compensation regimen may be provided by pressure support device 4 and the disordered breathing events may be detected by processing unit 24 based on outputs of one or more sensors such as flow sensor 22, pressure sensor 27, and/or proximate pressure sensor 28. Highlighted in FIG. 5 is a pressure compensation regimen 66 and corresponding series of disordered breathing events 68. Similar to FIGS. 3 and 4, the highlighted series of disordered breathing events 68 persist through the highlighted pressure compensation regimen 66. The highlighted pressure compensation regimen 66 and corresponding series of disordered breathing events 68 in FIG. 5 are additional examples of patterns which may trigger processing unit 24 to output the alert.

Figure 6:
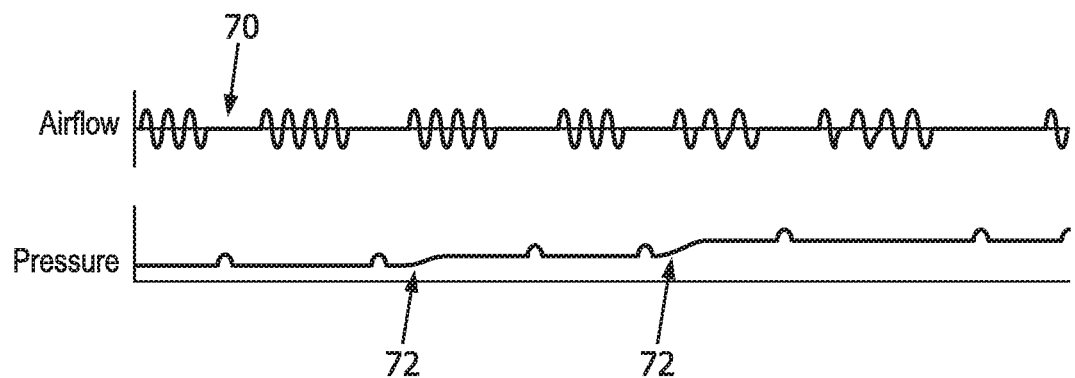
FIG. 6 is a graph of an airflow waveform and corresponding pressure compensation regimen in accordance with an example embodiment of the disclosed concept.

FIG. 6 is a graph of an airflow waveform of a patient and corresponding pressure compensation regimen in accordance with an example embodiment of the disclosed concept. The pressure compensation regimen may be provided by pressure support device 4 and the airflow waveform may be detected by processing unit 24 based on outputs of one or more sensors such as flow sensor 22, pressure sensor 27, and/or proximate pressure sensor 28. In FIG. 6, the bumps in the airflow waveform are test pulses that are provided to the airway. Because there is not airflow in response to the pressure test pulses, it can be determined that the airway is closed. Alternatively, if there was airflow in response to the pressure test pulses, it can be determined that the airway is open. It should also be noted that there are other methods known to those skilled in the art to test the patency of the patient's airway and it will be appreciated that such other methods may be employed in conjunction with the present concept.

It is also noted that the degree of patency of the patient's airway (i.e. the extent of closure, or the pressure-sensitivity of the closure) could be used to inform the decision to alert the patient. As the epiglottis is like a one-way valve, it is likely to not yield in response to a larger test pulse (e.g., a 10+cmH2O pressure pulse) and will show zero airflow, whereas a different site of collapse (e.g. soft palate) may show some smaller amount of airflow in response. A continued "no response" to larger pressure test pulses would be an early indicator of disordered breathing events that are unlikely to be responsive to pressure. Upon noting a very small (or zero) airflow response to test pulses of a certain size, an alert could be provided to the patient. In some embodiments, the alert may only be provided if the titrated pressure provided to the patient was already above a predetermined threshold.

Referring to FIG. 6, a disordered breathing event 70 (e.g., an apnea) occurs when airflow stops. As shown in FIG. 6, the disordered breathing event 70 occurs in a series that continues to persist and is not completely relieved by the pressure compensation regimen. The pressure compensation regimen includes increases in pressure 72. Despite the increases in pressure 72, disordered breathing event 70 persists. Processing unit 24 may, for example, determine that the pressure compensation regimen is not effective based on disordered breathing event 70 persisting through changes in the pressure compensation regimen.

Figure 7A:
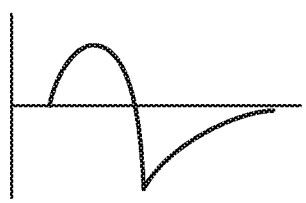
FIGS. 7A, 7B, and 7C are graphs of waveforms of a breath under different conditions in accordance with an example embodiment of the disclosed concept.
Figure 7B:
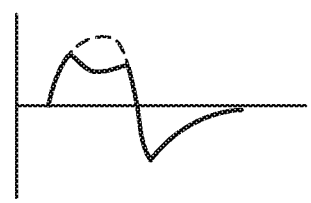
Figure 7C:
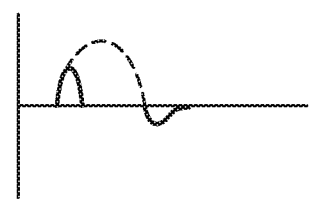

FIGS. 7A, 7B, and 7C are graphs of an airflow waveform of a patient for a single breath in accordance with an example embodiment of the disclosed concept. FIG. 7A is a waveform of an example of an airflow waveform for a nominal breath (e.g., no disordered breathing event). FIG. 7B is a waveform of an example of an airflow waveform for a breath during a soft palate collapse. FIG. 7C is a waveform of an example of an airflow waveform for a breath during an epiglottic collapse. FIG. 7C shows a short inhalation with a quick fall to zero airflow, much earlier than would be expected with a nominal breath, which is indicative of an epiglottic collapse. Processing unit 24 may output the alert based on detecting a waveform similar to that shown in FIG. 7C.

In some example embodiments, processing unit 24 may determine other sites of (and degrees of) airway closure (e.g. tongue base or vocal cords) that may be determinable from the airflow waveform and use that in determining whether the pressure compensation regimen is effective and whether output the alert (e.g., without limitation, a tongue base collapse may be more effectively treated by positional therapy).

Figure 8:
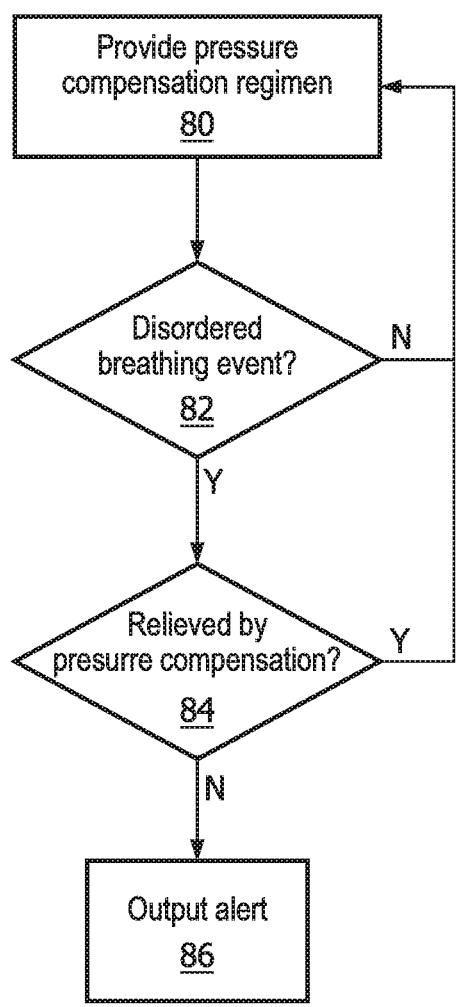
FIG. 8 is a flowchart of a method of providing an alert for non-effective pressure compensation regimen in accordance with an example embodiment of the disclosed concept.

FIG. 8 is a flowchart of a method of providing an alert for a non-effective pressure compensation regimen in accordance with an example embodiment of the disclosed concept. The method of FIG. 8 may be implemented, for example, by pressure support device 4 of FIG. 1. However, it will be appreciated that the method of FIG. 8 may also be implemented in other devices without departing from the scope of the disclosed concept. The method of FIG. 8 begins at 80 where pressure support device 4 provides a pressure compensation regimen to patient 10. At 82, processing unit 24 determines whether a disordered breathing event (e.g., an obstructive apnea) is present based on outputs of one or more sensors (e.g., flow sensor 22, pressure sensor 27, and/or proximate pressure sensor 28). If the disordered breathing event is not present, the method returns to 80 and pressure support device 4 continues to provide the pressure compensation regimen. However, if the disordered breathing event is present, processing unit 24 proceeds to 84 and determines whether the pressure compensation regimen is effective in relieving the disordered breathing event. Processing unit 24 may use any method described herein to determine whether the pressure compensation regimen is effective in relieving the disordered breathing event (e.g., without limitation, whether disordered breathing events persist for a predetermined period of time, whether disordered breathing events persist through changes in the pressure compensation regimen, etc.).

If processing unit 24 determines that the pressure compensation regimen is effective in relieving the disordered breathing event, the method returns to 80 and pressure support device 4 continues to provide the pressure compensation regimen. However, if processing unit 24 determines that the pressure compensation regimen is not effective in relieving the disordered breathing event, the method proceeds to 86 and processing unit 24 outputs the alert. The alert may be outputted using any method described herein (e.g., output to an indicator, output to an external device, etc.). It will also be appreciated that pressure support device may continue to provide the pressure compensation regimen through the method of FIG. 8 and continue to provide the pressure compensation regimen after the alert has been output.

It is contemplated that aspects of the disclosed concept can be embodied as computer readable codes on a tangible computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A pressure support device for providing pressure support therapy to a patient, the pressure support device comprising:
    a pressure generating system structured to generate pressure to provide pressure compensation to the patient via a patient circuit;
    one or more sensors structured to gather data indicative of disordered breathing events of the patient, wherein gathering said data includes sensing an airflow waveform for a number of breaths of the patient; and
    a processing unit structured to control the pressure generating system to provide a pressure compensation regimen to the patient and to deliver pressure test pulses to an airway of the patient; to analyze outputs of the one or more sensors while pressure support therapy is provided to the patient to determine if the pressure compensation regimen provided to the patient is effective to relieve one or more disordered breathing events, and to output an alert if it is determined that the pressure compensation regimen provided to the patient is not effective in relieving the one or more disordered breathing events,
    wherein, with respect to a given disordered breathing event, the processing unit is structured to determine a degree of patency of the airway of the patient associated with the given disordered breathing event,
    wherein the processing unit is structured to determine, as part of determining the degree of patency of the airway and in response to delivering a pressure test pulse exceeding a redetermined threshold pressure to the airway, that an epiglottic collapse has occurred in the patient if the airflow waveform shows zero airflow in response to delivery of the pressure test pulse,
    wherein the processing unit is structured to determine that an occurrence of epiglottic collapse cannot be addressed through titration of pressure of the pressure compensation regimen, and
    wherein the processing unit is structured to adjust one or more characteristics of the pressure compensation regimen, and wherein the processing unit is structured to determine that the pressure compensation regimen provided to the patient is not effective in relieving the one or more disordered breathing events when the one or more disordered breathing events persists through a predetermined number of adjustments to the one or more characteristics of the pressure compensation regimen.

2. The pressure support device of claim 1, wherein the processing unit is structured to determine that the pressure compensation regimen provided to the patient is not effective in relieving the one or more disordered breathing events when the one or more disordered breathing events persists for a predetermined period of time.

3. The pressure support device of claim 1, wherein the adjustments to the one or more characteristics of the pressure compensation regimen include an increase in the pressure compensation provided to the patient.

4. The pressure support device of claim 1, wherein the one or more disordered breathing events include an obstructive apnea.

5. The pressure support device of claim 1, further comprising:
    a communication unit;
    wherein, in response to the processing unit outputting the alert, the communication unit is structured to communicate the alert to an external device.

6. The pressure support device of claim 1, wherein the one or more sensors include one or more sensors structured to determine a body or head position of the patient, wherein the processing unit is structured to determine if the patient is in a supine position based on outputs of one or more of the sensors, and wherein the processing unit is structured to output the alert only if the it is determined that the patient is in the supine position.

7. The pressure support device of claim 1, wherein the alert includes a suggestion to use positional therapy.

8. The pressure support device of claim 1, further comprising:
    one or more indicators;
    wherein the one or more indicators are structured to provide one or more of a visual, an audible, and a tactile indication to the patient in response to the processing unit outputting the alert.

9. The pressure support device of claim 8, wherein the processing unit is structured to determine when the patient has aroused from sleep based on outputs of the one or more sensors, and wherein the processing unit is structured to wait until it has determined that the patient has aroused from sleep to output the alert.

10. A method of providing an alert for non-effective pressure compensation regimen, the method comprising:
    providing a pressure compensation regimen to a patient;
    receiving, with a processing unit, data from one or more sensors structured to gather data indicative of disordered breathing events of the patient, said data including airflow data for a number of breaths of the patient;
    determining, with the processing unit, if one or more disordered breathing events of the patient are present based on the gathered data;
    determining, with the processing unit, if the pressure compensation regimen provided to the patient is effective to relieve one or more disordered breathing events;
    determining, with the processing unit, a degree of patency of an airway of the patient associated with a given one of the disordered breathing events;
    delivering, with the processing unit, a pressure test pulse exceeding a predetermined threshold pressure to the airway of the patient;
    determining, with the processing unit, as part of determining the degree of patency of the airway, that an epiglottic collapse has occurred in the patient if zero airflow is detected in response to delivery of the pressure test pulse;

determining, with the processing unit, that an occurrence of epiglottic collapse cannot be addressed through titration of pressure of the pressure compensation regimen; and outputting an alert if it is determined that the pressure compensation regimen provided to the patient is not effective in relieving the one or more disordered breathing events, wherein providing the pressure compensation regimen to the patient includes adjusting one or more characteristics of the pressure compensation regimen with the processing unit, and wherein determining if the pressure compensation regimen provided to the patient is effective to relieve one or more disordered breathing events includes determining that the pressure compensation regimen provided to the patient is not effective in relieving the one or more disordered breathing events when the one or more disordered breathing events persists through a predetermined number of adjustments to the one or more characteristics of the pressure compensation regimen.

11. The method of claim 10, wherein determining if the pressure compensation regimen provided to the patient is effective to relieve one or more disordered breathing events includes determining that the pressure compensation regimen provided to the patient is not effective in relieving the one or more disordered breathing events when the one or more disordered breathing events persists for a predetermined period of time.

12. The method of claim 10, wherein the adjustments to the one or more characteristics of the pressure compensation regimen include an increase in the pressure compensation provided to the patient.

13. The method of claim 10, wherein the one or more disordered breathing events include an obstructive apnea.

14. The method of claim 10, wherein outputting the alert includes communicating the alert to an external device.

15. The method of claim 10, further comprising:
determining if the patient is in a supine position,
wherein outputting the alert includes outputting the alert only if the it is determined that the patient is in the supine position.

16. The method of claim 10, wherein the alert includes a suggestion to use positional therapy.

17. The method of claim 10, wherein outputting the alert includes providing one or more of a visual, an audible, and a tactile indication to the patient in response to the processing unit outputting the alert.

18. The method of claim 17, further comprising:
determining when the patient has aroused from sleep based on output of the one or more sensors, and
wherein outputting the alert includes waiting until the patient has aroused from sleep to output the alert.

19. A non-transitory computer readable medium storing one or more programs, including instructions, which when executed by a computer, causes the computer to perform a method of providing an alert for non-effective pressure compensation regimen, the method comprising:

providing a pressure compensation regimen to a patient;

receiving data from one or more sensors structured to gather data indicative of disordered breathing events of the patient, said data including airflow data for a number of breaths of the patient;

determining if one or more disordered breathing events of the patient are present based on the gathered data;

determining if the pressure compensation regimen provided to the patient is effective to relieve one or more disordered breathing events;

determining a degree of patency of an airway of the patient associated with a given one of the disordered breathing events;

delivering a pressure test pulse exceeding a predetermined threshold pressure to the airway of the patient;

determining, as part of determining the degree of patency of the airway, that an epiglottic collapse has occurred in the patient if zero airflow is detected in response to delivery of the pressure test pulse;

determining that an occurrence of epiglottic collapse cannot be addressed through titration of pressure of the pressure compensation regimen; and outputting an alert if it is determined that the pressure compensation regimen provided to the patient is not effective in relieving the one or more disordered breathing events, wherein providing the pressure compensation regimen to the patient includes adjusting one or more characteristics of the pressure compensation regimen, and wherein determining if the pressure compensation regimen provided to the patient is effective to relieve one or more disordered breathing events includes determining that the pressure compensation regimen provided to the patient is not effective in relieving the one or more disordered breathing events when the one or more disordered breathing events persists through a predetermined number of adjustments to the one or more characteristics of the pressure compensation regimen.

* * * * *